(12) United States Patent
Kittleson

(10) Patent No.: US 8,760,179 B2
(45) Date of Patent: Jun. 24, 2014

(54) HYDROCARBON VAPOR DETECTOR APPARATUS AND METHOD

(75) Inventor: Travis J. Kittleson, Mankato, MN (US)

(73) Assignee: Bosch Automotive Service Solutions LLC, Warren, MI (US)

( * ) Notice: Subject to any disclaimer, the term of this patent is extended or adjusted under 35 U.S.C. 154(b) by 736 days.

(21) Appl. No.: 12/914,721

(22) Filed: Oct. 28, 2010

(65) Prior Publication Data

US 2012/0105084 A1 May 3, 2012

(51) Int. Cl.
*G01R 27/08* (2006.01)

(52) U.S. Cl.
USPC .......................................................... 324/693

(58) Field of Classification Search
None
See application file for complete search history.

(56) References Cited

U.S. PATENT DOCUMENTS

| | | | | |
|---|---|---|---|---|
| 3,761,724 A | * | 9/1973 | Dennis | 340/517 |
| 4,025,324 A | * | 5/1977 | Stackhouse et al. | 96/111 |
| 4,827,246 A | * | 5/1989 | Dolan et al. | 340/521 |
| 5,079,944 A | * | 1/1992 | Boenning et al. | 73/23.4 |
| 5,150,603 A | * | 9/1992 | Boenning et al. | 73/31.05 |
| 5,281,816 A | * | 1/1994 | Jacobson et al. | 340/600 |
| 6,061,141 A | * | 5/2000 | Goldenberg et al. | 356/437 |
| 2006/0010974 A1 | * | 1/2006 | Koyano et al. | 73/431 |

* cited by examiner

*Primary Examiner* — Jermele M Hollington
(74) *Attorney, Agent, or Firm* — Baker & Hostetler LLP

(57) ABSTRACT

A hydrocarbon vapor detection instrument includes a hydrocarbon vapor detector, with conductivity proportional to contiguous airborne concentration of hydrocarbon vapor. The instrument further includes electronic circuitry providing an electrical signal proportional to the vapor detector conductivity and to a switch-selected sensitivity setting. The instrument further includes indicators to signal recharging status while a power switch is off and an external power supply is recharging the battery, namely that the battery is partially or fully charged and if the battery temperature is excessive, to signal that operating power is on, to signal that a low battery condition exists, and to signal different concentrations of hydrocarbon vapor. For the last of these, indicator position on a housing corresponds to vapor concentration. The instrument further includes an audible indication of power-on status and vapor concentration, changing with vapor concentration.

19 Claims, 9 Drawing Sheets

HYDROCARBON VAPOR DETECTOR APPARATUS AND METHOD

BACKGROUND OF THE INVENTION

1. Field of the Invention

The present invention relates generally to detection of hydrocarbon vapor in air. More particularly, the present invention relates to apparatus configured to sense selected concentrations of particular gases and to provide a user of such apparatus with information relating to the concentration of the particular gas or gases sensed.

2. Description of the Related Art

Several styles of detectors are available for use, for example, in the automobile repair industry. Such detectors include those for halogenated hydrocarbons, particularly air conditioning coolants, for carbon dioxide, for carbon monoxide, for unburned gasoline components in an exhaust stream, and for a variety of others. Automobile systems include other sensors, such as intake mass density, oxygen content in exhaust, and the like, that are used in conjunction with a processor to permit dynamic adjustment of fuel/air mixture, for example, in order to prevent preignition, compensate for altitude, etc.

Rapid detection of several relatively low specific gravity combustible gases at low concentrations is desirable and has been possible with varying success and convenience. Existing apparatus for this function may be physically large and/or heavy, may have relatively poor sensitivity in terms of concentration or variety of gases the apparatus can detect, may provide limited information regarding hazard severity, may respond slowly to changes in concentration, may halt operation with scant warning, may allow only short battery life, may require repeated replacement of short-lived single-use (i.e., primary) batteries, etc.

Any instrument in this general category that is to be used in work environments having potential to endanger health and life of users must be approved by a recognized testing agency for the country or geographic region of use. For example, in the United States, Underwriters Laboratories® is authorized to perform testing and certification that allows specific instruments to be used in workshops that operate under the purview of the U.S. Occupational Safety and Health Administration (OSHA) and certain other Federal agencies. Equivalent approvals are required in most countries or regions (the latter including the European Union).

What is desired in the art is a compact, highly sensitive combustible gas detection apparatus.

BRIEF SUMMARY OF THE INVENTION

The foregoing inadequacies of the art are overcome to a large extent by some embodiments in accordance with the present invention.

In one embodiment, a hydrocarbon vapor detection instrument is disclosed, whereof a property of conductivity is proportional to an airborne concentration of hydrocarbon vapor contiguous thereto. The instrument further includes an electronic circuit configured to provide an electrical signal, whereof the magnitude is proportional to the instantaneous conductivity of the vapor detector and to a sensitivity setting.

The instrument further includes a first plurality of indicators respectively configured to signal recharging status while an external power supply is connected and providing power to the battery and while the power switch is in an OFF position thereof, to signal that the battery is partially charged, to signal that the battery is fully charged, and to signal that the battery temperature is excessive. The instrument further includes a second plurality of indicators respectively configured to signal that operating power (VCC) is turned on and that a low battery condition is present or absent, and a third plurality of indicators respectively configured to signal different concentrations of hydrocarbon vapor detected by the hydrocarbon vapor detector, with spatial position of each on the housing corresponding to a relative vapor concentration indicated by its lighting. The instrument further includes an audible indicator of instrument status and vapor concentration, configured to produce an audio signal if operating power is on, the audio signal configured to change in the presence of a nonzero concentration of vapor, proportionately to the concentration of vapor.

In another embodiment, a method for detecting hydrocarbon vapor is disclosed. The method includes applying an electrical current to a sensor that has a conductivity that varies with a concentration of hydrocarbon vapor in a gas mixture applied to a surface thereof, generating a detected-hydrocarbon-vapor voltage proportional to a sensor conductivity voltage, offsetting the detected-hydrocarbon-vapor sensor conductivity voltage at least in part with a selected one of a plurality of discrete sensitivity threshold offset voltages, and activating any number of indicator display devices, wherein the number of indicators activated is proportional to the sensor-conductivity-proportional voltage, as offset by the selected discrete offset voltage.

There have thus been outlined, rather broadly, certain embodiments of the invention, in order that the detailed description thereof herein may be better understood, and in order that the present contribution to the art may be better appreciated. There are, of course, additional embodiments of the invention that will be described below, and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The above and other aspects and features of the present invention will become more readily apparent by describing in further detail exemplary embodiments thereof with reference to the accompanying drawings, in which.

DETAILED DESCRIPTION OF THE INVENTION

Figure 1:
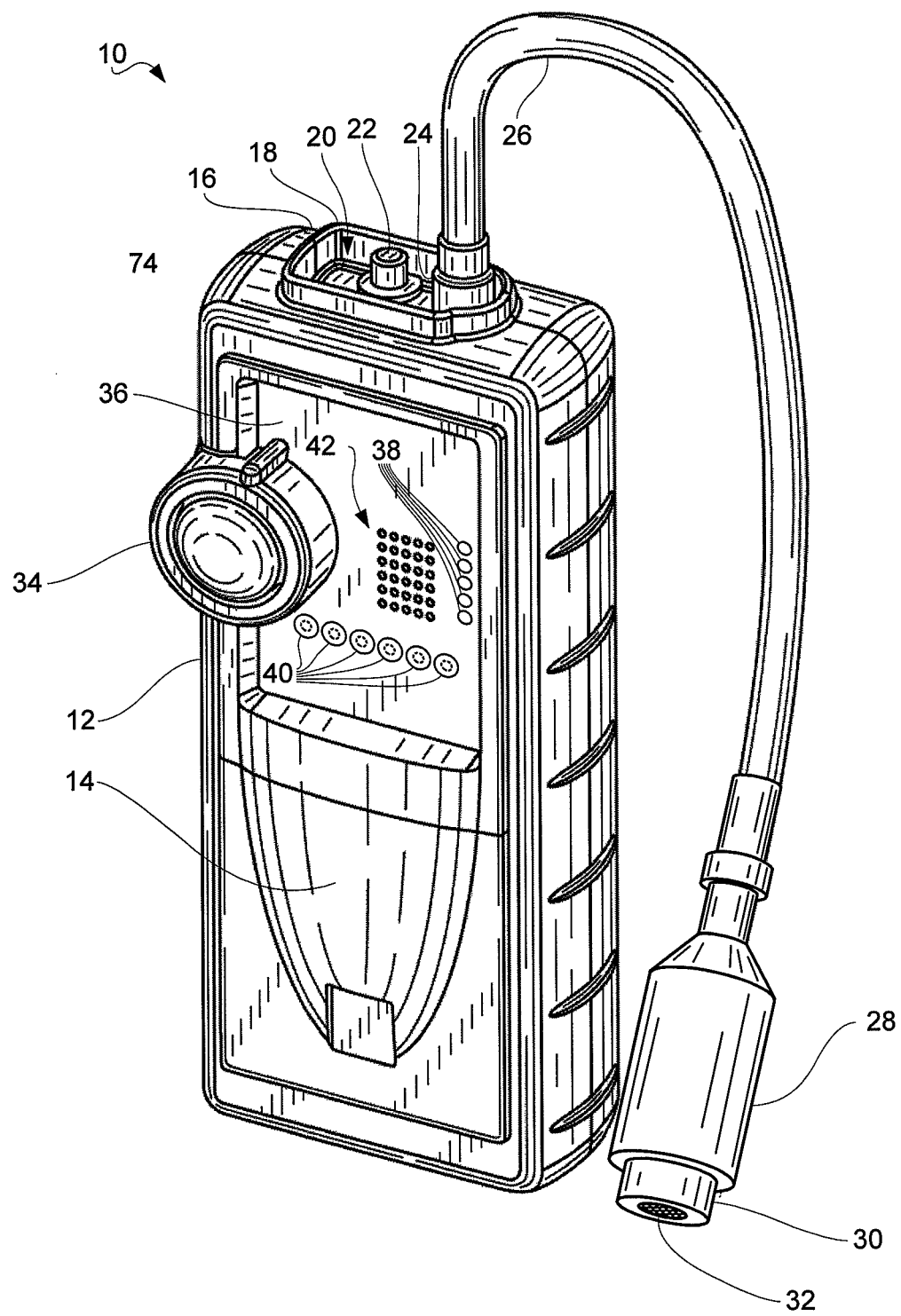
FIG. 1 depicts a perspective view of a hydrocarbon vapor detector in accordance with an embodiment of the present invention.

The general inventive concept will now be described more fully hereinafter with reference to the accompanying drawings, in which various example embodiments are shown. This invention may, however, be embodied in many different forms, and should not be construed as limited to the embodiments set forth herein. Rather, these embodiments are provided so that this disclosure will be thorough and complete, and will fully convey the scope of the invention to those of ordinary skill in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower" can, therefore, encompass an orientation of lower and/or upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass an orientation of above and/or below.

Unless otherwise defined, all terms (including technical and scientific terms) used herein have the same meaning as commonly understood by one of ordinary skill in the art to which this invention belongs. It will be further understood that terms such as those defined in commonly-used dictionaries should be interpreted as having a meaning that is consistent with their meaning in the context of the relevant art and the present disclosure, and will not be interpreted in an idealized or overly formal sense unless expressly so defined herein.

Exemplary embodiments are described herein with reference to illustrations that are schematic illustrations of idealized embodiments. As such, variations from the shapes of the illustrations, as a result, for example, of manufacturing techniques and/or tolerances, are to be expected. Thus, embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Embodiments of the present invention may provide detection capability for any of a plurality of hydrocarbons in vapor form (i.e., hydrocarbons in a gaseous state, mixed into ordinary air, dry nitrogen, or a user-preferred test gas mixture, at typical environmental temperatures and pressures or over a user-preferred range of conditions). Other vapors—ones not detectable by the particular sensor incorporated in the embodiment shown herein, such as carbon monoxide, other poisonous or noxious gases, etc.—may be detectable by apparatus differing primarily in its sensor, in threshold voltages associated with the sensor, in sensitivity ranges and step values appropriate to the sensor, etc. Other apparatus incorporating the invention may detect particulates or other classes of airborne materials, for example. Detectable concentration of an airborne substance is dependent on chemical properties of the substance and on sensitivity of a selected detector component with respect to that substance's physical chemistry. In order to realize consistent detection sensitivity, a detector component may include a temperature-regulated heater along with a sensor. Conductivity of some types of sensors is low in the absence of hydrocarbon vapor. Upon introduction of a hydrocarbon vapor above a basal concentration into ambient air contiguous to a detector of a type characterized by responsiveness to that hydrocarbon, conductivity of some sensors increases. Sensor conductivity may vary somewhat with ambient air pressure, humidity, and other environmental factors, as well as over a sensor's service life and in response to exposure to corrosive agents or other factors leading to degradation.

Embodiments incorporating the invention can provide visible and audible indication of hydrocarbon concentration. In some embodiments, as concentration increases, a series of light emitting diode (LED) indicators illuminate, with a first LED lighting at a low level, and additional ones lighting at a series of step increments in concentration. For example, a sensitivity adjustment in some embodiments is configured to apply an offset to the level at which the LED representing the lowest concentration lights, with the remaining LEDs lighting with the same step increments relative to the first for all sensitivity settings. Each such step may provide activation of a visible indicator of another type in other embodiments. The audible indication in these and/or other embodiments can be a continuous train of short tone bursts, running at approximately two such tone bursts per second. Each tone burst may last about 45 milliseconds, with a fundamental tone around 2500 Hz, approximating a square wave, so that there are small and diminishing even and odd harmonics in the tone, producing a somewhat mechanical effect, rather than, for example, a musical or pure-tone sound. It is to be understood that alternative audible signals may be implemented with similar effect, such as a continuous audio tone that rises in frequency and/or volume with concentration, or silence in the absence of detectable vapor concentration, etc. Likewise, a tone burst with the indicated parameters is one of many embodiments, including warbles, chirps, etc., readily implemented using a variety of devices. It will be shown that the tone burst is relatively economical of battery power, but other considerations, such as audibility at low levels in noisy environments, uniqueness, etc., may bear on sound selection. In most instances over the remainder of the present disclosure, the term "tick" or "tick sound" is used in lieu of "tone burst," since this suggestive term succinctly describes the audible effect created by the circuit in the embodiment shown.

Detector circuitry in at least some embodiments uses a conventional analog operational amplifier integrated circuit (IC) device (hereinafter op amp) to detect the output of specific types of sensors. The circuitry in the embodiment shown uses a novel application of known passive components to provide multiple sensitivity and strength ranges, and a novel combination of components to realize a unique apparatus.

FIG. 1 shows a perspective view of a hydrocarbon vapor detection instrument 10 that incorporates an embodiment of the inventive apparatus. The instrument 10 includes a housing 12 enclosing a circuit board (not visible) and a battery (not visible), the latter concealed by a removable access cover 14. The instrument 10 further includes a top plate 16 having a surrounding rim 18 within which a recess 20 restricts inadvertent contact with an alternate action (i.e., push-on, push-off) pushbutton power switch 22 and a mechanical coupling fitting 24 for a flexible, position-retaining, insulated and resilient-surfaced wand 26, the wand 26 having at its distal end a bulb 28 in which a detector 30 is carried. Terminating the detector 30 is a grille 32 (just visible at the end of the bulb 28 distal to the housing 12) that allows subject gases to pass freely over the sensor surface of the detector 30.

The instrument housing 12 in the embodiment shown in FIG. 1 includes a user-accessible knob 34 that can be rotated to any of a plurality of detent-defined angular positions to select a setting for a rotary switch (the switch itself is internal and thus not visible) that controls instrument sensitivity. A front plate 36 has a vertical row of portals 38 through which can be viewed lighted LEDs that indicate a concentration of hydrocarbons according to the detector 30. The height of the column of lighted LEDs represents both the setting of the sensitivity switch actuated via knob 34 and the detected concentration of hydrocarbons. A horizontal row of portals 40 shows lighted indications of status of several instrument functions. LEDs are used for all lighting functions in the embodiment shown. A matrix of holes 42 in the housing 12 and front plate 36 allows passage of acoustical signals from an audio transducer (the audio device is internal and thus not visible).

Like the vertical row of LEDs, the acoustical signals provide an indication of vapor concentration. Note that the indicated "portals" and "holes" for visual and audible signal transmission may be simple holes, transparent regions, etc. in some embodiments. For example, patterns of holes in a housing 12 can be covered using a thin, optically and/or acoustically transparent front plate 36, itself coated with an opaque film over much of its surface. Such an arrangement can provide a feature such as a barrier against contaminants with little decrease in visual and acoustic performance.

At developer option, sensitivity level setting may use any of a variety of user-operated selector styles, such as a row of pushbuttons wherein pressing one causes that one to remain pressed and releases any other previously pressed, or a momentary-contact switch pair providing up/down control through a range of settings, for which the selected setting may be displayed separately, or another selector style. In other embodiments, sensitivity level may be fixed, may be continuously variable under user control, or may be adjusted by the instrument with or without user interaction.

At developer option, the component parts assembled to form the housing 12, battery cover 14, and top plate 16 may be fabricated from any of a variety of materials. A typical material that may be satisfactory for this application is injection molded acrylonitrile butadiene styrene (ABS), a thermoplastic copolymer of the named constituents having good electrical and mechanical properties. This material can be toughened by reinforcement with fiber or other filler agents and treated with additives that enhance resistance to ultraviolet (UV) light (primarily sunlight) and pollutants. Color can be included; some colorants may have good resistance to fading. A resilient "boot" structure that surrounds the housing 12 at least at its corners can be incorporated, and may decrease component stress resulting from physical abuse.

Figure 2:
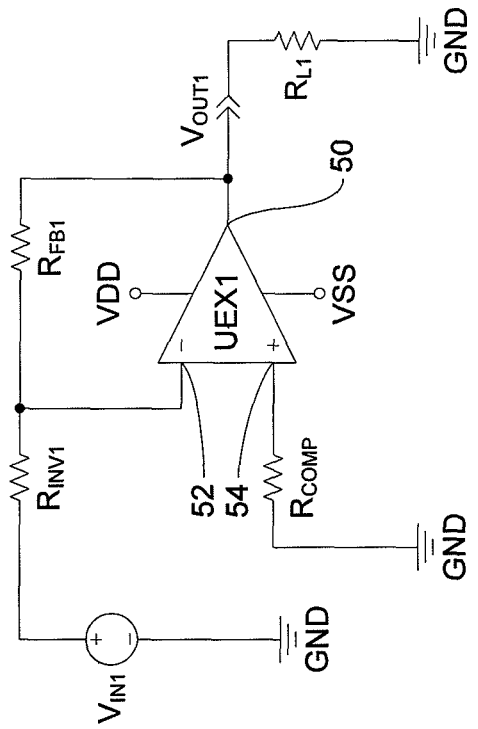
FIG. 2 depicts a generic inverting operational amplifier configuration.

Explanation of Operation of Inverting Amplifier Shown in FIG. 2

FIG. 2 presents a related application for an op amp UEX1 in which an applied signal is amplified and inverted in polarity. In this application, resistor $R_{FB1}$ can be described as providing negative feedback. An alternate term of reference can describe $R_{FB1}$ as furnishing a conduction path from the output node 50 of the op amp UEX1 to the inverting input node 52, the latter marked with a minus sign ("−"). Typical op amp UEX1 internal circuitry (not shown) is configured to adjust its unitary output node 50 voltage until sufficient current flows into any attached load $R_{L1}$ to develop a voltage across that load $R_{L1}$ and further to drive the inverting input node 52 to the same voltage as the non-inverting input node 54 (the latter marked with a plus sign ("+")).

Inverting-node input resistor $R_{INV1}$ is placed to connect a signal source $V_{IN1}$, further described below, to the inverting input node 52. A ground (GND)-referred input signal from an ideal voltage source $V_{IN1}$ is conducted through the input resistor $R_{INV1}$. The voltage of the applied signal with reference to the voltage present on the non-inverting input node 54 forces a particular value of current through input resistor $R_{INV1}$. This current exactly offsets the feedback current from the output node 50 through the resistor $R_{FB1}$, holding the inverting input node 52 at the same voltage as the non-inverting input node 54.

For the non-inverting input node 54 to be stable, a connection is made from that node 54 to a ground reference GND in the circuit of FIG. 2. Various op amp types have better or worse internal compensation circuitry, so a well-established practice in the art is to make the connection from the non-inverting input node 54 to GND through a compensation resistor $R_{COMP}$ as shown. $R_{COMP}$ may be zero or any non-zero value, with varying success, but preferentially has a resistance equal to that presented on the inverting input node 52. The $R_{INV1}$ and $R_{FB1}$ resistors have a Thévenin equivalent $R_{TH1}$ (specifically, their parallel value, noting that the op amp output 50 impedance is effectively zero, and the signal source $V_{IN1}$ is defined as ideal, i.e., likewise having zero impedance) that is readily computed; $R_{COMP}$ preferably has a value close to $R_{TH1}$, selected from available components.

Put in other words, the signal present on the out put node 50 is equal to the arithmetic inverse of the input signal $V_{IN1}$, multiplied by a gain term equal to the ratio of the resistances of $R_{FB1}$ and $R_{INV1}$. Summed with this to form the signal on the output node 50 is an offset term from the non-inverting input node 54. In the generic circuit of FIG. 2, the op amp UEX1 may have a complementary power supply (not shown) in which a first power supply output (VDD) is positive with respect to GND, and a second power supply output (VSS) is negative with respect to GND, and of magnitude approximately equal to and tracking VDD. This enables op amp UEX1 output node 50 to swing above and below ground as dictated by its inputs and by open-loop and closed-loop gain. Output voltage swing is limited by the magnitudes of VDD and VSS and further limited by op amp UEX1 output stage positive-going and negative-going saturation voltages. Op amp saturation voltages are typically specified by manufacturers as "rail to rail" or somewhat narrower. With the non-inverting input resistor $R_{COMP}$ connected to GND, the non-inverting offset is zero, and the circuit output is $V_{OUT1}=-V_{IN1}*(R_{FB1}/R_{INV1})$. This statement does not apply to circuits wherein appreciable reactive or other nonlinear components introduce gain variation with frequency or voltage—that is, filter functions using capacitors and/or inductors, knee functions using diodes in input or feedback paths, etc.

Figure 3:
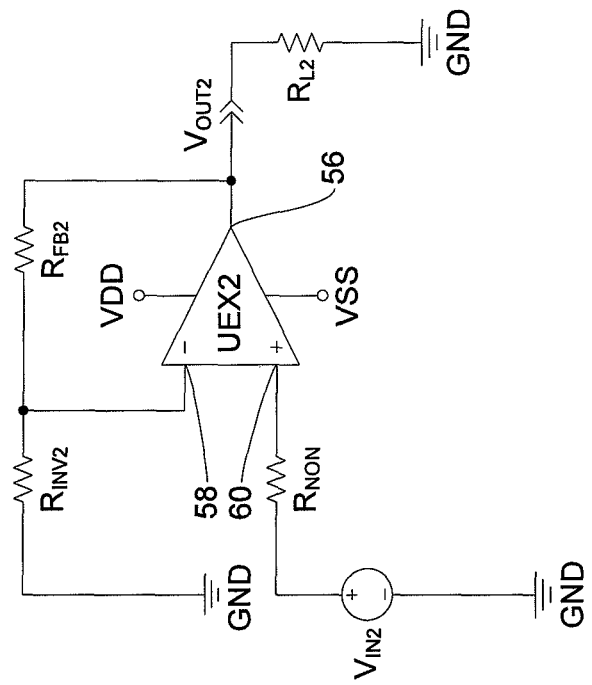
FIG. 3 depicts a generic non-inverting operational amplifier configuration.

Explanation of Operation of Non-Inverting Amplifier Shown in FIG. 3

FIG. 3 presents a related application for an op amp UEX2 in which an input signal $V_{IN2}$ is amplified, but is not inverted in polarity. The signal on the output node 56 is equal to the input signal $V_{IN2}$ applied to the non-inverting resistor $R_{NON}$, multiplied by a non-inverting gain. With the inverting resistor $R_{INV2}$ connected to any ideal voltage source, such as GND in a complementary-supply configuration as shown, the non-inverting gain at the output 56 for input signal $V_{IN2}$ is one greater than (and opposite in polarity to) the inverting gain of the circuit of FIG. 3—that is, $V_{OUT2}=V_{IN2}*(1+R_{FB2}/R_{INV2})$. Note that the value of resistance of the non-inverting input node resistor $R_{NON}$ does not affect circuit gain for a broad range of input resistor values, although it is again preferable for many op amp types to have the resistance of $R_{NON}$ approximate the value of $R_{FB2}$ and $R_{INV2}$ in parallel, balancing the input bias currents. As in the inverting case discussed above, this statement does not apply to circuits wherein nonlinear components introduce gain variation.

Explanation of Operation of Sensor Voltage Amplifier

Figure 4:
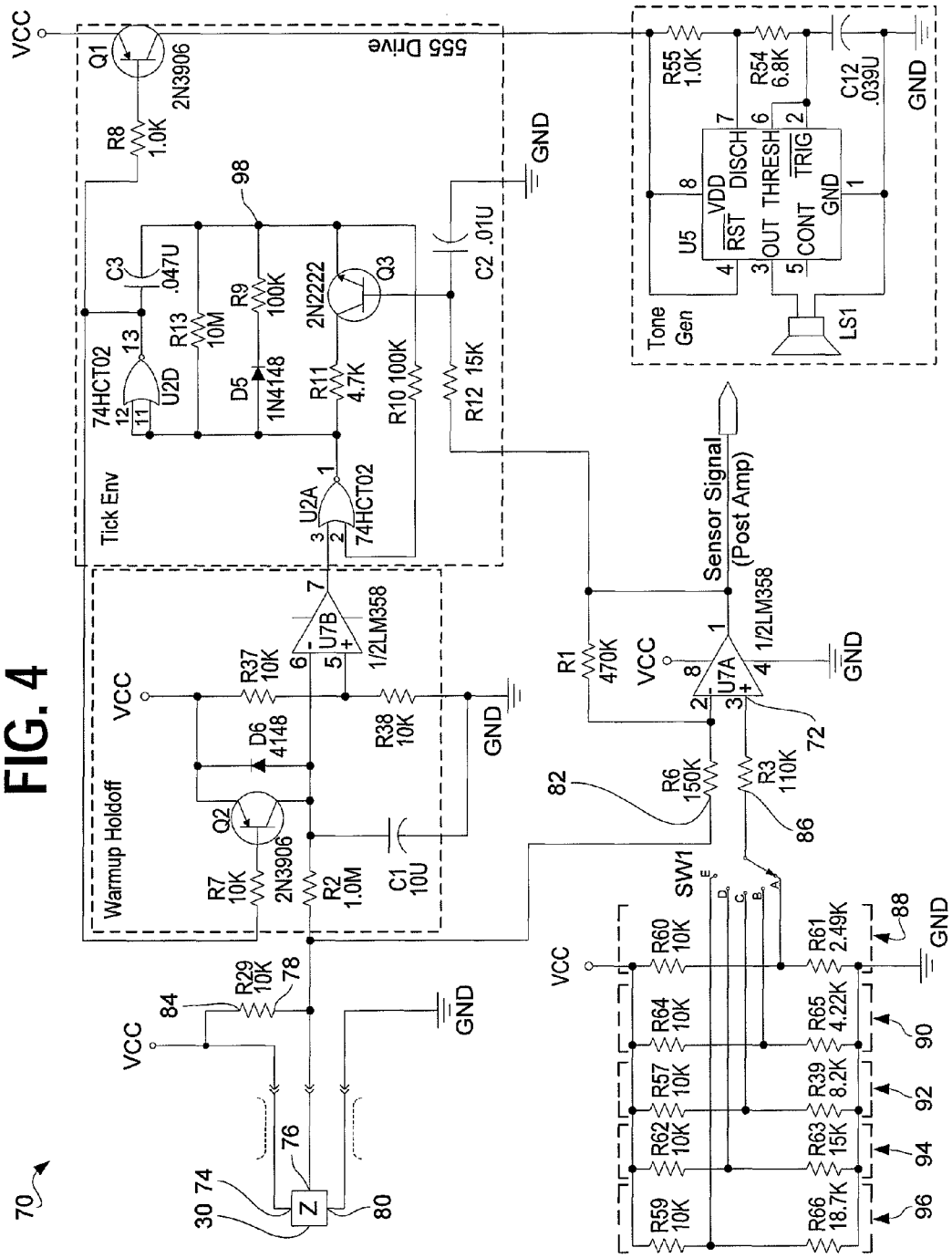
FIG. 4 depicts an operational amplifier, sensitivity control circuitry, and related details, in accordance with embodiments of the present invention.

In all discussion that follows, "U," "R," "C," "B," "SW," and other prefix mnemonics and their associated numbers are those used in specific manufacturer schematics and apply to unique components within this specification. FIG. 4 presents an embodiment using a dual op amp, U7, of which one section, U7A, is presented first, with U7B operation discussed below. This circuit 70 combines attributes of the circuits shown in FIGS. 2 and 3, as applied to embodiments of the invention. In the circuit of FIG. 4, a single positive power supply VCC is referred to ground (GND), instead of using a dual, complementary supply as in FIGS. 2 and 3. Reference voltages intermediate to VCC and GND are needed in many such single-supply circuits. Such a reference voltage is applied to op amp non-inverting input node U7 pin 3. In the instant embodiment, a series of selectable references are established at junction points between voltage divider resistors, connected in pairs between VCC and GND. Use of reference dividers is a generally practical and reliable design strategy that can be less costly and/or more reliable than providing a dual-supply or split-supply circuit.

It is well established that passive components (resistors, capacitors, etc.) have manufacturing tolerances, so that each sample has an assigned value with an uncertainty due at least to random variation within a stated range, variation with temperature and age, etc. Active components (op amps, discrete semiconductors, etc.) likewise have tolerances in their parameters. While any analog circuit design may have a nominal performance, each instantiation of that design is built from finitely-exact components, and has a particular performance determined by the accumulated tolerances of its parts. All discussions of circuit performance herein are made with an assumption of uncertainty regarding the actual performance of a specific instantiation of an embodiment, both as initially manufactured and as performance may drift in response to age, temperature variation, and other stresses.

In using a single-supply design, it is well-established practice for the designer to consider all of the signal swings resulting from every signal inversion. In the embodiment shown in FIG. 4, it is possible for applied signals to cause one or more op amp inputs or outputs to be driven to one of the extreme positive (VCC) or negative (GND) supply levels, commonly referred to as the power supply "rails," which may also be associated with saturation of one of the output transistors of the op amp. The effect of such "overdrive" on product performance, and on the specific ability of a selected op amp type to tolerate this without degradation, is preferably to be taken into consideration. For example, an op amp type of which an output circuit is capable of latching up when one of its inputs is driven to a rail could be viewed as unacceptable for a design, or could be made usable with a guard circuit that can prevent either the input overdrive or the output latchup. Likewise, an op amp that draws abruptly greater current with its output driven into saturation could shorten battery run time, or could overheat, shortening component life. It is generally sufficient to thoroughly analyze normal and worst-case behavior in view of the component vendors' data sheets, and to build and test prototypes, including application of thermal stress. In addition to testing and worst-case analysis, methods for design validation include so-called Monte Carlo simulation, wherein large numbers of software simulations of circuit operation are executed with pseudorandom assignment of values of various components within their respective tolerance ranges. Response of a simulation to such alterations, examined for anomalies, may point to design flaws, component limitations, etc.

In other embodiments, it may be preferred to use a dual-power-supply configuration (usually but not exclusively having regulated, complementary positive-voltage and negative-voltage power rails) that can include a ground reference common to and intermediate between the supplies, or to use a configuration with a single negative-voltage power supply. In the latter, the VCC terminal of the op amp shown would be set instead to the ground-referred terminal of the power supply, and the GND terminal would be set instead to the (negative) output of the power supply. In still other embodiments, operational amplifier functionality may be realized using an op amp portion of a mixed-signal IC device, user-programmable or otherwise, or an analog comparator or function generator IC. An embodiment may include one or more ICs, each of which includes one or a plurality of op amp functional units therein; the embodiment shown is an example of using dual-op-amp ICs.

Similarly, comparable functionality may be realized by digitizing or synthesizing the indicated analog signals and performing the indicated operations using time-domain digital signal processing (DSP) by means of one or more dedicated DSP devices, a general-purpose computer, etc., or by converting between time-domain digital signals and frequency-domain representations thereof as desired. The embodiment described in detail herein is thus one of many functionally equivalent embodiments contemplated for the invention.

In still other embodiments, programming of the "sensitivity" function through the use of pairs of divider resistors and a selector switch SW1, as shown, may be replaced with other arrangements. Alternative sensitivity setting arrangements may include, for example, a single string of resistors from VCC to GND, with the switch SW1 tapping off a desired value, or a programmable linear voltage reference similar to U10, but using a switch-selectable combination of programming resistors to set the voltage, and thus the detection sensitivity, or a stepwise-variable "digital potentiometer," user-controlled with a step-up/step-down programming switch. It may be observed that sensitivity resistors arranged in pairs as in the embodiment shown have steps, and thus sensitivity switch settings, that are independent of one another in part.

As shown in FIG. 1, the embodiment has a flexible, position-retaining, insulated wand 26 allowing a detector 30, which is a fingertip-sized cylinder, to be located approximately a quarter to a half of a meter (a foot, more or less) away from the device housing 12. Returning to FIG. 4, the detector 30 (the device is shown in the schematic circuit diagram 70 as a connectorized "black box" three-terminal component) has a first terminal 74 connected to VCC, a second terminal 76 connected to a first terminal 78 of a pullup resistor $R_{29}$, and a third terminal 80 connected to GND. The detector second terminal 76 is also connected to the input terminal 82 of the inverting-node input resistor $R_6$. Pullup resistor $R_{29}$'s second terminal 84 is connected to VCC. Resistor $R_{29}$ has a relatively small resistance value compared to $R_6$ in the op amp circuit, limiting $R_{29}$'s effect on static circuit properties such as DC gain.

Embedded within the detector 30 is a heater element (not shown), connected between the first and third terminals 74 and 80 thereof. Also located within the detector 30 is a detector element (also not shown separately) connected between the second and third terminals 76 and 80 thereof. When power is applied, the heater element rises to a particular self-regulating temperature after a time delay that depends on atmospheric temperature and on any cool-down time that may have passed since the last use of the instrument 10. The temperature-regulation function of the heater is selected from methods familiar in the art, and is not subject to further disclosure herein. The conductivity of the sensor element depends on the temperature of its surroundings, as regulated by the heater, and on the air density and the concentration of detectable hydrocarbon vapor in the air proximal to the sensor element. This is a combination of trade secret and publicly known practices for the detector device, and is not subject to further disclosure herein, other than values of sensor conductivity while in use.

In practical use, a detection instrument may be subjected to "nuisance tripping," that is, having signals indicating the presence of hydrocarbons that are not of concern to a user. For example, in automobile engine repair work, small amounts of gasoline may be present but be viewed as unimportant to a repair technician, while in a laboratory test environment, very slight traces of acetone could be quite serious. In order to address such variations, the embodiment shown includes a sensitivity baseline adjustment in the form of a series of step settings. A user can select a sensitivity that avoids nuisance indications while assuring that any level of concentration that is of actual interest is brought to attention quickly. Since a user may be looking away from the instrument, such a sensitivity adjustment can be applied to the circuit at a point prior to the visual and aural detectors, ensuring that it affects both indications.

The non-inverting input resistor 3 input terminal 86 is connected to one of several reference circuits 88, 90, 92, 94, and 96 through position A, B, C, D, or E, respectively, of a multiple-position selector switch SW1. Each reference circuit in the embodiment shown uses a pair of resistors connected in series from VCC to GND. The point of connection between the resistors in each pair has a Thévenin equivalent output voltage and source impedance that are readily computed using known methods. The Thévenin equivalent resistance of the reference circuit selected through the switch SW1 adds in series with the resistance of non-inverting input resistor $R_3$. All values of the summed input resistance preferably approximate the resistance seen on the inverting input node, U7 pin 2. As may be noted readily, the reference resistors in the embodiment shown have relatively small resistance values compared to $R_3$, limiting their influence on static circuit properties such as DC gain.

In the absence of traces of hydrocarbon vapor detectable by its sensor, the detector 30 has approximately zero conductivity between sensor terminals 76 and 80, so the signal present at the input terminal 82 of $R_6$ is effectively VCC, with a source impedance approximating the resistance of pullup resistor $R_{29}$. As the concentration of hydrocarbon vapor within the detector 30 increases, sensor conductivity as measured between terminals 76 and 80 increases, so that the current flowing through pullup resistor $R_{29}$ increases. This increases the voltage drop across $R_{29}$, so the signal applied to the $R_6$ input terminal 82 decreases from near VCC toward GND. It will be noted that the effective installed source impedance of the sensor in combination with $R_{29}$ is always at or below the value of $R_{29}$ alone, namely 10 K ohms in the embodiment shown, while $R_6$ has a nominal value of 150 K ohms. The effect of the sensor and pullup $R_{29}$ on circuit gain is small in the embodiment shown, on the order of 2%-5% over the range of sensor circuit operation ordinarily of interest, in which sensor current is on the order of 70 microamps to 500 microamps.

The sensor signal is multiplied by the (inverting) gain of the U7A circuit; this is summed with a switch-selected sensitivity offset voltage applied to the non-inverting node U7 pin 2 (multiplied by the non-inverting gain in that signal path) to yield an output that appears at the op amp output terminal, U7 pin 1. This is summarized for selected values of sensor voltage and for all SW1 switch positions in TABLE 1.

TABLE 1

Output at Various Switch Settings and Sensor Readings

| Sensor Voltage | Op Amp Output (Volts) vs Sensitivity Switch SW1 Position | | | | |
|---|---|---|---|---|---|
| | A | B | C | D | E |
| 4.73 | GND | GND | GND | GND | 0.07 |
| 4.30 | GND | GND | GND | 0.13 | 1.24 |
| 4.00 | GND | GND | GND | 1.02 | 2.13 |

TABLE 1-continued

Output at Various Switch Settings and Sensor Readings

| Sensor Voltage | Op Amp Output (Volts) vs Sensitivity Switch SW1 Position | | | | |
|---|---|---|---|---|---|
| | A | B | C | D | E |
| 3.50 | GND | GND | GND | 2.51 | 3.63 |
| 3.19 | GND | GND | 0.19 | 3.44 | 4.56 |
| 3.00 | GND | GND | 0.76 | 4.01 | 5.14 |
| 2.55 | GND | GND | 2.11 | 5.39 | VCC |
| 2.00 | GND | 0.4 | 3.79 | VCC | VCC |
| 1.50 | GND | 1.94 | 5.34 | VCC | VCC |
| 1.00 | 1.33 | 3.49 | VCC | VCC | VCC |
| 0.60 | 2.58 | 4.75 | VCC | VCC | VCC |
| 0.30 | 3.52 | VCC | VCC | VCC | VCC |

Values for sensor output voltage higher than 4.73 volts, which is the first sensor voltage listed in TABLE 1—that is, levels of sensor conductivity less than that necessary to draw sufficient current to pull resistor $R_{29}$ down to the highest voltage level in the table—do not cause op amp output on U7 pin 1 to rise above its negative-going saturation voltage, even with the sensitivity setting at maximum. Put another way, for all sensitivity settings, when the sensor draws 0.07 mA or more current, the amplifier U7A comes out of negative-going saturation.

The sensitivity input term supplied through SW1 applies a second signal component, this one to the non-inverting input, scaled by the non-inverting gain. Changing the SW1 sensitivity setting results in a shift in both op amp input nodes U7 pin 2 and U7 pin 3 and in the op amp output node U7 pin 1, so that the sensitivity adjustment term is effectively summed with the sensor measurement.

Display Threshold LED Drivers

Figure 5:
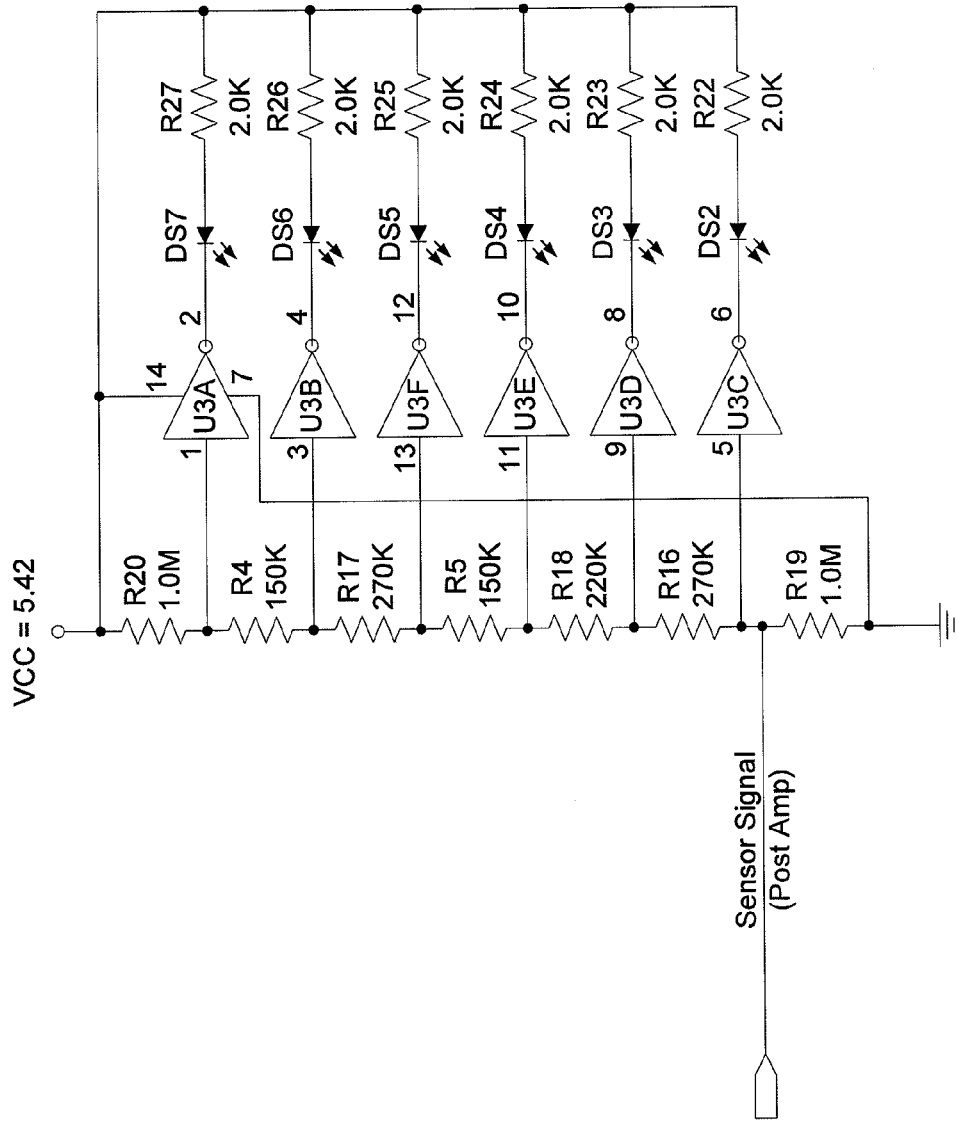
FIG. 5 depicts threshold LED indicator circuitry, in accordance with embodiments of the present invention.

FIG. 5 shows a resistor string $R_{20}$, $R_4$, $R_{17}$, $R_5$, $R_{18}$, $R_{16}$, and $R_{19}$, with the op amp output voltage from U7 pin 1 applied to the $R_{16}/R_{19}$ junction, and with the top of the string connected to VCC. Associated inverting digital logic buffers, U3A, U3B, U3F, U3E, U3D, and U3C connect at the junctions between adjacent resistors. As sensor conductivity increases due to the presence of hydrocarbon vapor, the sensor signal voltage applied to the $R_6$ input node 82 drops toward GND, in response to which the additive component of the op amp output voltage on U7 pin 1 due to detection becomes increasingly positive.

As the U7A output—the scaled sum of the sensor and sensitivity terms—rises, it eventually exceeds 50% of VCC for each inverting buffer U3A, U3B, U3F, U3E, and U3D in succession. As the signal does this, each buffer's respective output U3 pin 2, U3 pin 4, U3 pin 12, U3 pin 10, and U3 pin 8 switches from a high state to a low state, drawing current from VCC through resistors $R_{27}$, $R_{26}$, $R_{25}$, $R_{24}$, and $R_{23}$, respectively, and powering LED indicators $DS_7$, $DS_6$, $DS_5$, $DS_4$, and $DS_3$, respectively. The respective trip points follow Table 2, assuming VCC=5.42 volts, with $DS_7$ lighting at the lowest detector 30 signal level and $DS_3$ at the highest.

TABLE 2

Nominal Sensor Signal and Internal Thresholds

| LED | Amplifier Output Signal for Turnon (Volts) | Quiescent Level (Volts) |
|---|---|---|
| $DS_7$ | 0.57 | 3.08 |
| $DS_6$ | 1.20 | 2.73 |
| $DS_5$ | 1.60 | 2.10 |
| $DS_4$ | 2.34 | 1.75 |
| $DS_3$ | 2.71 | 1.33 |
| $DS_2$ | 3.44 | 0.60 |

$DS_2$ in the embodiment shown operates differently from $DS_3$-$DS_7$. The $DS_2$ threshold is independent of the rest of the string, so U3 pin 6 switches to a low state when the U7A output exceeds 3.44 volts for VCC=5.42 volts, irrespective of the state of the other display components. For each sensitivity setting, a specific sensor voltage activates $DS_2$. The combinations of sensor voltages and switch settings are tabulated in Table 3. $DS_3$-$DS_7$ likewise have specific thresholds for all switch settings, proportional to the voltages shown for $DS_2$.

TABLE 3

Threshold Signal for DS2 to Light

| SW1 Switch Setting | Sensor Voltage |
|---|---|
| A | 0.323 |
| B | 1.02 |
| C | 2.11 |
| D | 3.19 |
| E | 3.56 |

All voltages given herein were computed using nominal values for resistances and active circuit device properties, and omit losses associated with resistance of wires, circuit traces, connectors, etc. It is to be understood that normal manufacturing variation may produce results for any defect-free sample according to the embodiment shown that differ from these values, but are acceptable in view of system requirements. Component tolerances are to be assigned and test parameters specified to ensure detection of product defects and meet end-user requirements.

Warmup Function

Returning to FIG. 4, a warmup holdoff circuit is shown. The detector 30 is calibrated at a temperature elevated above ordinary room temperature, and includes a heater as described above to ensure that the sensor output will be constant over an allowed range. A holdoff function is used to suppress audible alarm sounding for roughly 10 seconds after application of power. U7B, the second section of U7, has an equal-value voltage divider $R_{37}$ and $R_{38}$ that sets a threshold of 2.71 volts on the U7B non-inverting input terminal U7 pin 5. The RC time constant of $R_2$ and $C_1$ holds the inverting input node U7 pin 6 low, placing a high (VCC less the internal drop of the op amp) on U2 pin 3, one of the inputs of NOR gate U2A, causing the NOR gate's output to go low (above GND by the HCT output drive saturation voltage). This feeds NOR gate U2D, which is configured as an inverter, the output of which is thus high, ensuring that $Q_1$ and $Q_2$ remain cut off and suppressing both output tones and U2 oscillation during the warmup time delay.

At the end of the warmup time delay, and in the absence of a significant detector 30 signal, U7B inverting input node U7 pin 6 rises higher than non-inverting input node U7 pin 5, reversing the state of the feed to U2 pin 3 from U7 pin 7. From that time forward, the state of U2D is controlled by the state of U2 pin 2, which is the other input to U2A—that is, the signal from $R_{10}$. In addition, during each "tick" during normal (post-warmup) operation, as discussed below, transistor $Q_2$ momentarily applies a pull-up signal on capacitor $C_1$, maintaining the "high" state applied to op amp inverting input node U7 pin 6, and keeping U7B disabled until the instrument is turned off.

Tick Generator

FIG. 4 also shows a two-part circuit that generates a pulse envelope and a tone. The first part is the free-running oscillator introduced above, which uses U2A, U2B, $C_3$, $R_{13}$, $D_5$, $R_9$, $R_{11}$, $Q_3$, and $R_{10}$. This oscillator runs at a baseline rate of approximately 2 Hz with a duty cycle of approximately 1%. That is, the signal appearing on U2D output pin 13 is high, cutting off transistor $Q_1$, for about ½ second, after which pin 13 is pulled low for about 4.7 msec, and then goes high again. This circuit also responds to a detected sensor signal on U7 pin 1, modulated by the sensitivity circuit. As a combination of detected hydrocarbons and elevated sensitivity raises the U7 pin 1 output voltage, the oscillator pulse rate increases. This pulse rate increase may also be described as a shortening the duration of each "high" output period that leaves the low-state signal duration roughly constant. The op amp U7 pin 1 output controls the voltage applied to transistor $Q_3$ base. Prior to the expiration of the warmup period, $Q_3$ collector is driven to a TTL low level by U2A NOR output U2 pin 1, so $Q_3$ emitter is cut off.

As noted above, after the warmup holdoff circuit $R_2C_1$ junction voltage rises higher than the $R_{37}/R_{38}$ divider junction voltage, the warmup holdoff output on U7 pin 7 switches from a high-state saturation, about 1.2 volts below VCC, to a low-state saturation, about 0.8 volts above GND. Both of these levels represent valid logic state inputs for the U2 device in the embodiment shown. If the second U2A input, pin 2, is already at GND, then the U7B transition causes the U2A output pin 1 to switch to VCC. U2D output pin 13 then switches to GND, coupling a short (4.7 msec, approximately ½₀₀th of a second) negative-going pulse through $C_3$ to $Q_3$ emitter and the other components connected thereto at a common tie point 98. Timing of this pulse is controlled by $D_5$ conduction, which causes $R_9$ to replace $R_{13}$ as the resistance discharging $C_3$, drawing the second U2A input pin 2 above 50% of VCC, reversing the states of U2A and U2D, and terminating the pulse. With $D_5$ now cut off, $R_{13}$ controls the charge timing of $C_3$ at about ½ second. The cycle then repeats.

This establishes a train of negative-going pulses (i.e., from VCC to GND) that make up the envelope of the audio signal. Turning on $Q_1$ applies power to the 555 timer U5, which then runs at a (nominally) 2534 Hz rate until the pulse ends, which occurs after about 12 cycles of near-square wave. Timing follows standard criteria for a 555 timer configured as an astable multivibrator. Buried window comparator reference signals at ⅓ VCC and ⅔ VCC are generated within the 555 by three matched resistors in the 555 that form a voltage divider. Application of power allows $C_{12}$ to charge through the series string of $R_{55}$ and $R_{54}$. When the charge level on the THRESH/TRIG node (U5 pins 2 and 6) exceeds ⅔ VCC, the internal state reverses, the OUT node (U5 pin 3) goes to GND, and the DISCH node (U5 pin 7) grounds the $R_{55}/R_{54}$ junction. $C_{12}$ then discharges through $R_{54}$ alone; when the falling THRESH/TRIG node reaches ⅓ VCC, the internal state reverses again, releasing the DISCH node so that $R_{55}$ and $R_{54}$ can recharge $C_{12}$. After a first, double-length ON period, low and high output durations are $t_{LO}=\ln(2)*C_{12}*R_{54}$ and $t_{HI}=\ln(2)*C_{12}*(R_{55}+R_{54})$; the operating frequency is $f_C=1/(t_{HI}+t_{LO})$.

The OUTPUT node swings between approximately VCC and GND, depending on the technology in which the 555 is implemented and on the output load. The OUTPUT node signal is applied to a speaker, LS1. In other embodiments, an audio transducer with an integral oscillator apparatus can be used in place of the timer and speaker, with a tradeoff that many such transducers do not permit users to select a preferred or distinctive sound. In still other embodiments, the 555 can be left powered on, with the RESET pin 4 used to gate the speaker drive signal. In yet other embodiments, use of a 555 implemented in CMOS (LMC555, TLC555, CSS555, AU7555, ICM7555C, TS555I, etc.) or another low-power technology (XR-L555, etc.) in place of a conventional TTL-style device may reduce battery power consumption. It is to be noted that the configuration in the embodiment shown, by applying and removing power from U5, produces zero power consumption except during each tone burst, and thus incorporates at least a step toward power minimization.

The combination of the U2A/U2D/$Q_3$ circuit and the $Q_1$/U5 circuit produces a continuous stream of short tone bursts, roughly two per second, during normal operation of the detector, in the absence of detected hydrocarbon vapor. As the sensor detects increasing concentrations of such materials, the voltage at the sensor signal "post amp" output node U7 pin 1, and thus the base drive and conductivity of $Q_3$, increase, shunting the $R_{13}$ wait time control resistor and the $D_5$ and $R_9$ pulse envelope time control circuit. As long as the effective resistance of $R_{11}$ and $Q_3$ remains appreciably greater than that of $R_9$, the envelope waveform timing remains substantially constant. Once the combination of sensitivity threshold setting and concentration of sensed level of hydrocarbon vapor becomes high enough, the wait time between pulses grows shorter, with the high-state and low-state output durations determined by $C_3$ and $R_9$ in parallel with $R_{11}$ and $Q_3$, and by the internal parameters of the TTL-compatible, H-series CMOS gate U2D.

Battery Charger Control

Figure 6:
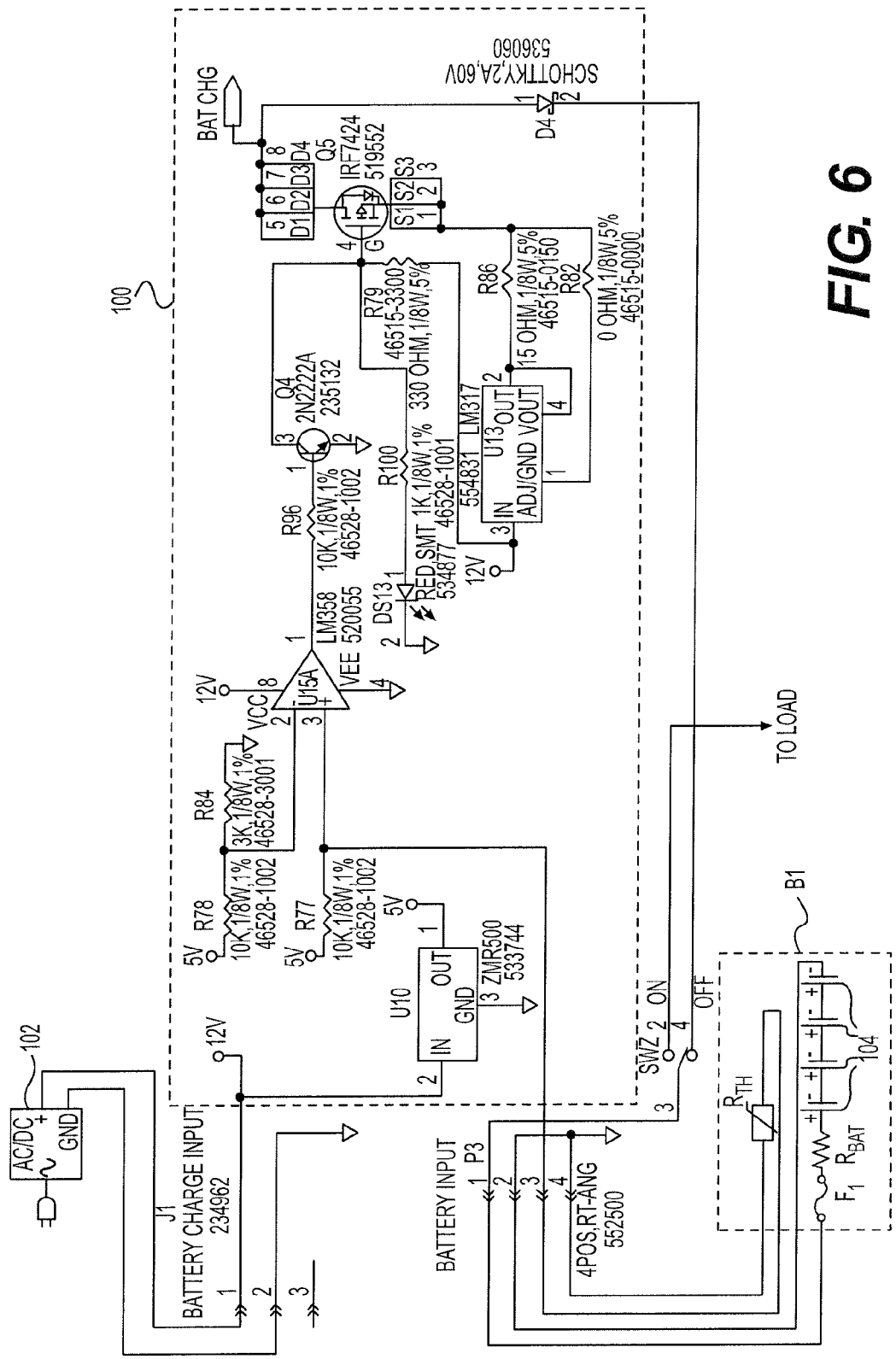
FIG. 6 depicts battery charging and related circuitry, in accordance with embodiments of the present invention.

FIG. 6 shows the battery charger control circuitry 100. An external DC power supply 102 with a nominal 12 volt output can be connected to the embodiment shown. It is to be understood that any combination of individual cells, whether configured as a single unit or electrically interconnected externally to the envelope of each to furnish a single source of voltage, is customarily termed a "battery," and that the term "secondary battery" is applicable for any battery type that can be discharged and recharged a plurality of times, distinct from a "primary battery," for which the internal chemistry is not designed for recharging. For example, nickel metal hydride (NiMH) cells can be connected to form a secondary battery, whereas so-called alkaline cells are primary, and are directed to be disposed of after discharge.

When a switch SW2 is placed in the "OFF" position as shown, which is also the charge position, the battery assembly B1 is disconnected from the remaining circuitry in the instrument, and connected to the charger control circuitry 100. In the absence of a charger 102 supplying DC power, the "OFF" position of the switch SW2 causes the instrument to do nothing, with the Schottky diode $D_4$ isolating the battery assembly B1 from the remainder of the charger control circuitry 100. With both the charger 102 and the battery assembly B1 connected and the charger 102 providing voltage, a three-terminal regulator U10 generates a 5 volt power signal applied to several voltage dividers, while the raw 12 volts is applied as chip power to op amp U15A, as well as to a second three-terminal regulator U13, the latter configured to act as a constant current source at 0.083 amps when a load is connected.

The charger circuit 100 load is the battery assembly B1. The charger circuit 100 is switched by a MOSFET $Q_5$ based on charger 102 availability and battery cell 104 temperature.

When battery charging current from the current source U13, $R_{86}$ is enabled, current passes through MOSFET $Q_5$, the Schottky diode $D_4$, the switch SW2, and connector $P_3$ terminals 1 and 2, then to the cablized battery assembly B1. A fuse $F_1$ and a 4 ohm series resistor $R_{BAT}$ inside B1 are connected in series with the four NiMH cells 104 in the embodiment shown. The fuse $F_1$ is rated approximately 0.75 A and has a voltage drop approximating 70 mv under charging conditions; the resistor $R_{BAT}$ drops approximately 0.332 v during charge. Omitting losses in the connectors and wiring, this adds a total drop during charging of about 0.4 v to the drops in the charger circuit 100.

Significant in the embodiment is the choice of a charge rate that assured to be harmless to the battery under all non-failure conditions. The industry criterion for this is a so-called "C/20" or "C over twenty" rate. C is the battery capacity in ampere hours, and a rule of thumb us that a charge rate of one twentieth of the capacity per hour does not appreciably shorten battery life. That is, the C/20 charge rate can be tolerated indefinitely without harming cell chemistry. For the particular cells in this design, the C/20 rate is 0.1 amps. The design rate of 0.083 amps is less than C/20, and worst-case components can also be shown to be harmless.

Additional connector terminals $P_3$-3 and $P_3$-4 connect to a thermistor $R_{TH}$ that is mechanically coupled to the battery cells 104, so that it is maintained at substantially the same temperature as the cells 104. A pullup resistor $R_{77}$, powered from the three-terminal regulator U10, provides current to the thermistor $R_{TH}$. As the battery cell 104 temperature changes, the thermistor $R_{TH}$ resistance changes more rapidly than the $R_{77}$ resistance, so that the pullup resistor $R_{77}$ and the thermistor $R_{TH}$ form a voltage divider with a temperature-dependent voltage. A second voltage divider powered from the same regulator U10 has two relatively stable and well-matched resistors $R_{78}$ and $R_{84}$ that hold a substantially constant setting of approximately 1.15 volts. As long as the battery temperature remains below 61° C. (142° F.), the charge control circuit is enabled, with the thermistor $R_{TH}$ resistance falling exponentially as the temperature rises. Above the indicated temperature, voltage applied to the op amp section U15A non-inverting input U15 pin 3 falls below that applied to inverting input U15 pin 2, and output U15 pin 1 changes from a high voltage to a low voltage. Note that the op amp section U15A is used as a comparator, has gain and slew rate limited by its internal properties, and has no external hysteresis connection. As its inputs reverse relative magnitude, U15A switches from being saturated about 1.2 volts below VCC to being saturated about 0.8 volts above GND.

It is to be understood that the temperature shutdown threshold of 61° C. (142° F.) inside the instrument is quite high, not normally occurring except after a cell reversal or other failure event. The overtemperature protection function is thus primarily intended to ensure that the instrument itself is intrinsically safe, which is the first criterion for any safety instrument.

The output of op amp section U15A drives the base of bipolar transistor $Q_4$ through resistor $R_{96}$. When U15A output pin 1 is in its high-voltage state, $Q_4$ is driven into conduction and pulls MOSFET $Q_5$ gate low, causing $Q_5$ likewise to conduct. The on-state resistance of $Q_5$ is a fraction of an ohm, so its voltage drop is negligible. As noted above, Schottky diode $D_4$ drops about 0.3 volts. The internal circuitry of the regulator U13 realizes a dropout voltage of no more than about 1.5 volt at this low current. The series resistor $R_{86}$ that establishes the current regulation level drops about 1.25 volts. As indicated above, the battery assembly B1 drops another approximately 0.4 volts during charge. Thus full current from regulator U13 is applied to the stacked cells 104 of the battery assembly B1 at any necessary voltage up to 8.6 volts, with in-line losses limited to about 3.5 volts.

Figure 7:
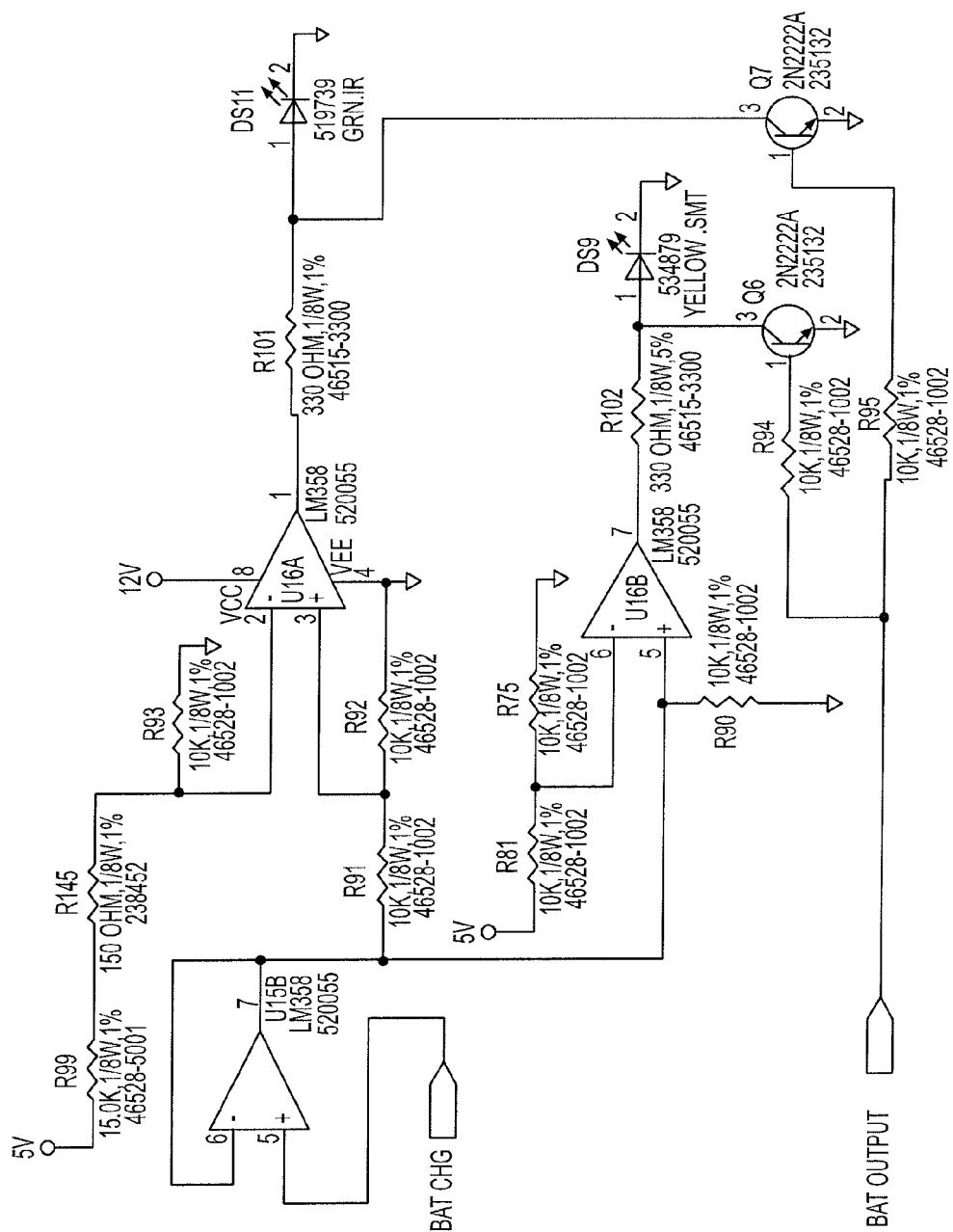
FIG. 7 depicts battery charge level monitor circuitry, in accordance with embodiments of the present invention.

FIG. 7 shows a second (and last) section of op amp U15, configured as a (non-inverting) voltage follower, connected to track the voltage of the current applied to the battery assembly B1 (BAT CHG, sampled above the Schottky diode $D_4$, and thus about 0.7 volts more positive than the cell stack 104 voltage), and, with a low output impedance, exhibiting negligible voltage error. This tracking signal is applied to two comparator sections U16A and U16B, which have voltage dividers applied to their inverting inputs. $R_{99}/R_{145}/R_{93}$ provide a nominal 3.3 volt reference to U16A; $R_{81}/R_{75}$ provide a nominal 2.5 volt reference to U16B. Once the cell stack 104 charge exceeds about 1.9 volts, yellow LED $DS_9$ turns on. The U15B voltage follower output is divided in half by $R_{91}$ and $R_{92}$, so the 3.3 volt reference is effectively 6.6 volts. Once the cell stack 104 charge exceeds about 5.9 volts, green LED $DS_{11}$ turns on. If the switch SW2 is put in the "ON" position, the battery is disconnected from the charge circuit, and transistors $Q_6$ and $Q_7$ are turned on, which lowers the voltage across $DS_9$ and $DS_{11}$ to about 0.2 volts, extinguishing them even if they would otherwise be turned on by the presence of the charger 102. In the absence of an external charger, $Q_6$ and $Q_7$ draw no current.

Switch-Mode Power Supply

Figure 8:
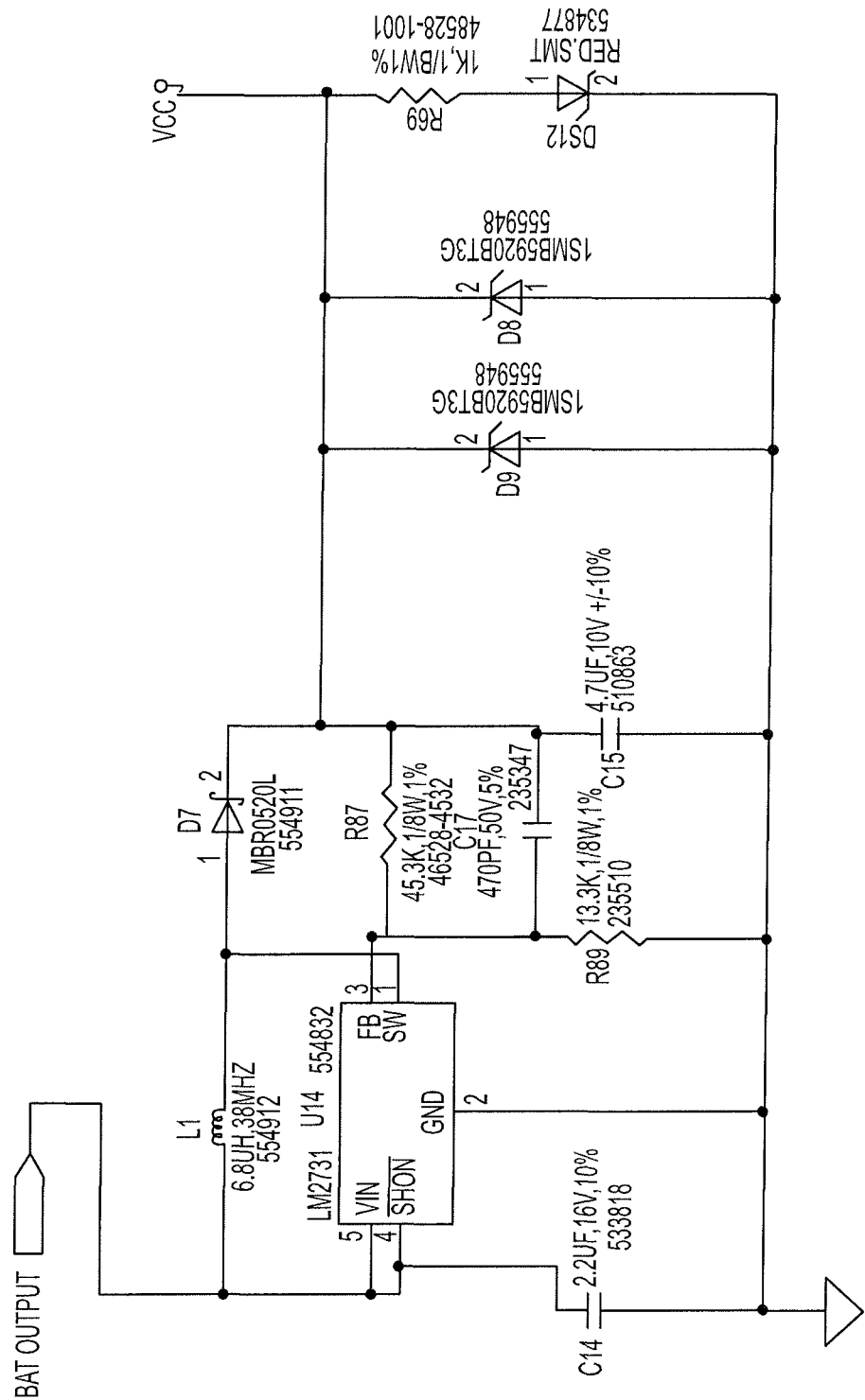
FIG. 8 depicts switch-mode power supply circuitry, in accordance with embodiments of the present invention.

FIG. 8 shows a switch-mode power supply circuit that includes special-purpose boost converter device U14 and its associated passive components. This design is generally conventional, except as noted. The output voltage is regulated by the ratio of $R_{87}$ to $R_{89}$, which gives it a nominal value of 5.42 volts over a range of battery voltage from the battery's maximum down to about 2.7 volts. The maximum is a function of battery chemistry and the number of cells in the battery, and is approximately 4.8 volts in the embodiment shown. The switch-mode power supply output is 5.42 volts in the embodiment shown, which is appreciably higher than the nominal 5.00 volts (the value realized by resistor pair listed in the chip vendor's published application notes), to allow a battery with a nominal 4.8 volts full-charge voltage to operate with a boost-only converter for every worst-case combination of components. Device U14 internally-set oscillator frequency is fixed for each of two models. The model in the embodiment shown operates at 580 KHz. This and other representative designs can exhibit a relatively low noise content in the output voltage, even with modest filtering. Noise may be dependent on loading, with higher drawdown of capacitor stored charge during the discharge portion of each boost cycle serving to increase output voltage excursions and thus the magnitude of at least the fundamental component of the oscillator frequency when highly loaded. Low battery state may also increase capacitor drawdown and thus noise.

Zener diodes $D_8$ and $D_9$ are redundant, 6.2 volt+/−5%, 3 watt devices connected across the output of the switch-mode power supply. The devices are specified so that either alone can prevent cascading circuit faults from elevating circuit temperature to a hazardous level.

In alternative embodiments, a buck-boost converter able to provide 5.0 volts, 3.3 volts, or another desirable output voltage for a battery voltage that starts above the desirable output voltage and drops below that level in use, such as the somewhat less efficient, fixed-output Texas Instruments TPS63002DRC, or a similar device, may be preferred. Such a device may be able to keep the VCC voltage further below logic IC absolute maximums, if preferred. In addition, although generally deprecated for new products, linear regulators, battery-based unregulated power, and other technologies may be preferred for specific applications, just as the linear references and regulators used in the embodiment shown may be replaced by additional switch-mode devices in still other embodiments. For any such embodiment, a user may elect to assign different values to some of the divider-generated reference voltages.

Low Battery Detection and Display

Figure 9:
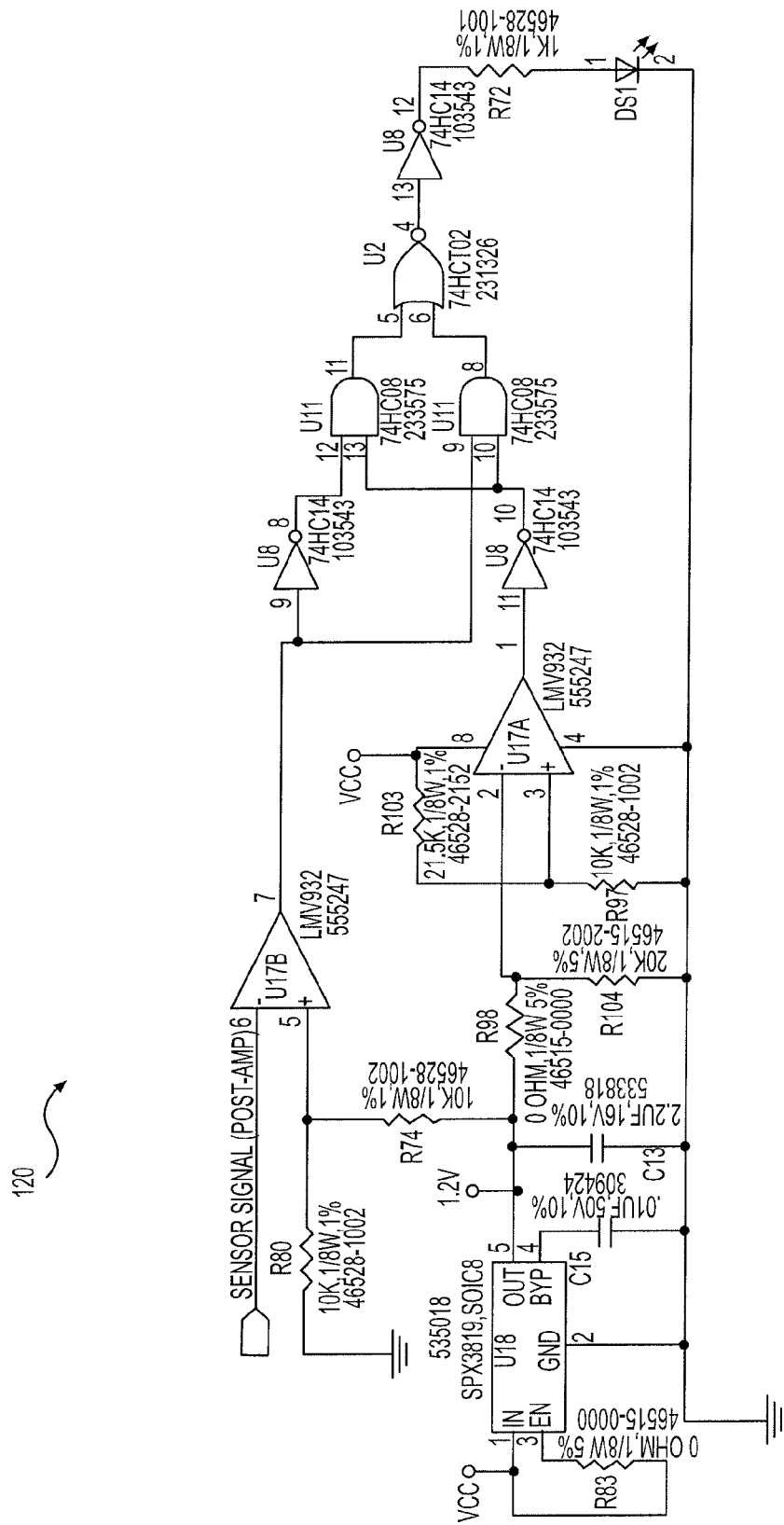
FIG. 9 depicts low-battery status detection circuitry, in accordance with embodiments of the present invention.

FIG. 9 shows a circuit 120 for detecting low battery level. As noted above, the boost converter switching regulator of FIG. 8 is able to accept a battery voltage over a useful range and output a voltage raised to a fixed level with minor noise content. A cell stack 104 such as the NiMH type shown in the embodiment can provide nearly constant current into a fixed load as cell voltage slowly decreases. At some battery charge level, however, the cell stack 104 voltage exhibits much more rapid decrease with time at the same loading—graphed as a "knee" in some references and referred to as "going off a cliff" by some practitioners. Meanwhile, the boost converter 100 gradually increases its current demand with a fixed output load (current times voltage) as the available voltage from the battery decreases. Ultimately, at some threshold in battery voltage, the boost converter output voltage VCC begins to decrease. The result of this is a fairly abrupt collapse of output voltage from the boost converter, typically when the battery discharge is on a fairly steep part of the knee portion of its discharge curve.

The embodiment is configured to detect an appreciable decrease in boost converter output voltage at a stage in battery discharge at which the battery and boost converter retain a combined usable life of about a half-hour of full-usability drive to the instrument, and more if lightly loaded. This "usable life" designation includes high sensor current (high concentration of hydrocarbons), high pulse rate for output sounds, and large numbers of LEDs turned on. At this point (controlled in part by battery temperature), a circuit causes a battery charge status LED, $DS_1$, to light, using the following process.

In a first mode of operation, a low-dropout positive regulator U18 provides a nominal 1.2 volt signal as long as VCC remains above a specified threshold—commonly on the order of 0.5 volts above the U18 regulator output voltage. Thus, as long as VCC is above about 1.7 volts, the U18 reference signal remains available. The signal is applied to U17 pin 2, the inverting input of an op amp configured as a comparator. The VCC signal itself is divided down by $R_{103}$ and $R_{97}$ and this scaled voltage, 1.72 volts, is applied to U17 pin 3, the non-inverting input of U17A. When VCC droops so that the U17 pin 3 input falls below 1.2 volts, which occurs when VCC falls below 3.78 volts (for nominal component values), U17 pin 1 output switches from high to low. The logic tree using gates of U8, U11, and U2 lights the $DS_1$ LED.

In a second mode of operation, when the Sensor Signal (Post-Amp) applied to U17 pin 6, the inverting input of U17B, is above a specified threshold, namely 0.6 volts in the embodiment shown, this is assumed to indicate that there is sufficient signal to need continuous reporting, even if the battery voltage is drooping. Consistent with this assumption, the embodiment disables the low battery indication and prevents $DS_1$ from lighting. As noted above, this mode remains operational for approximately 30 minutes, which is assumed to be longer than the normal duration of a sensed hydrocarbon event. At any time during such an event, the loss of the detected sensor signal will allow the low battery indication to be activated.

Block Diagram

Figure 10:
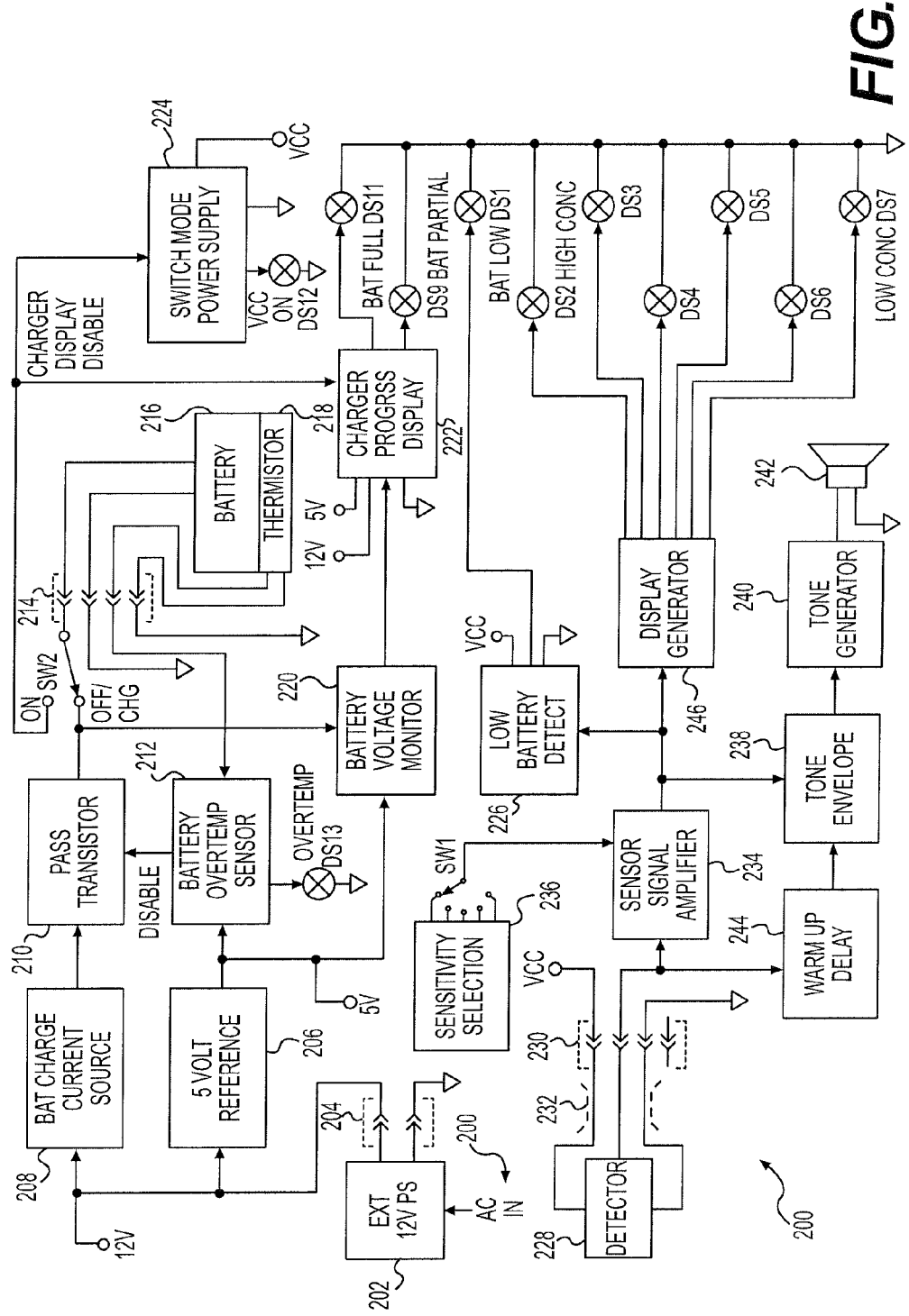
FIG. 10 depicts an embodiment of the invention in block diagram form.

The above functions are summarized in block diagram form in FIG. 10. The diagram shows that an external AC source 200 powers an external 12 volt power supply 202. Through a connector 204, this 12 V DC is applied to a 5 volt reference 206 and a battery charger current source 208. The current source 208 output drives a pass transistor 210 except when the pass transistor is disabled by a battery overtemperature sensor circuit 212. The pass transistor 210 output is directed through a switch SW2, in its OFF/CHG position, through a connector 214, to a battery assembly 216. Attached to the battery assembly 216 is a thermistor 218. The thermistor 218 is coupled to the overtemperature sensor circuit 212 via the same connector 214 used by the battery assembly 216. A battery voltage monitor circuit 220 provides status indications to a charger progress display driver circuit 222.

When the switch SW2 is in the ON position, power from the charger circuitry 200, 202, 204, 206, 208, and 210 is disconnected from the battery assembly 216 and power from the battery assembly 216 disables the charger progress display circuit 222 and is applied to a switch mode power supply circuit 224, producing sensor instrument working voltage VCC. VCC is applied to a low battery detection circuit 226. VCC is also applied to a detector 228 through a connector 230 and wand 232. The detector 228 sensor signal is applied to a sensor signal amplifier 234, controlled in part by a sensitivity selection circuit 236, accessed via a sensitivity selection switch SW1. The sensor signal amplifier 234 output is applied to a tone envelope circuit 238, which drives a tone generator circuit 240, the output of which is directed to a speaker 242. The tone envelope circuit 238 is disabled during a warmup period by a warmup delay circuit 244. The sensor signal amplifier 234 output is also directed to the low battery detection circuit 226, the low battery status signal of which is disabled by a high level on the sensor signal amplifier 234 output. The sensor signal amplifier 234 output is also directed to a display generator 246.

Output indications from the instrument are audible, in the case of the speaker 242, which produces no output during battery charge and during warmup delay, a continuous series of short click or tick signals at a roughly 2 Hz rate during normal operation with no detectable concentration of hydrocarbons present, and the same ticks at an increasing rate as the concentration of hydrocarbons increases above a minimum threshold for each hydrocarbon type. Visual indications of battery status during charging are provided by lighting of LEDs for battery partially full $DS_9$, battery full $DS_{11}$, and battery overtemperature $DS_{13}$. Visual indications of instrument status during normal operation are provided by lighting of LEDs for VCC on $DS_{12}$ and battery low $DS_1$. Visual indications of hydrocarbon concentration above the minimum threshold are provided by lighting of LEDs $DS_7$, $DS_6$, $DS_5$, $DS_4$, $DS_3$, and $DS_2$ for successively greater concentrations, in the order indicated, consistent with the increasing tick rate on the speaker 242. LEDs with reference designations $DS_8$ and $DS_{10}$ are not used in the embodiment disclosed herein.

Typical hydrocarbons can be detectable by an instrument embodiment in at least the concentrations indicated in Table 4.

TABLE 4

| Detectable HC thresholds | |
|---|---|
| HC Type | Concentration (PPM) |
| Acetone | 50 |
| Acetylene | 50 |
| Gasoline | 1 |
| Isobutane | 100 |
| Propane | 50 |

What I claim is:

1. A hydrocarbon vapor detection instrument comprising:
a hydrocarbon vapor detector having a property of conductivity that is proportional to an airborne concentration of hydrocarbon vapor contiguous with the detector;
an electronic circuit configured to provide an electrical signal having a magnitude proportional to an instantaneous conductivity of the hydrocarbon vapor detector and to a sensitivity setting;
a first plurality of indicators respectively configured to signal recharging status while an external power supply is connected and providing power to a battery and while a power on/off switch is in an OFF position, to signal that the battery is partially charged, to signal that the battery is fully charged, and to signal that a battery temperature is excessive, wherein the power on/off switch is user-accessible from outside a housing and having a power-off state and a power-on state;
a second plurality of indicators respectively configured to signal that operating power (VCC) is turned on and that a low battery condition is present or absent;
a third plurality of indicators respectively configured to signal different concentrations of hydrocarbon vapor detected by the hydrocarbon vapor detector, with spatial position of each on the housing corresponding to a relative vapor concentration indicated by its lighting; and
an audible indicator of instrument status and vapor concentration, configured to produce an audio signal if operating power is on, the audio signal configured to change in the presence of a nonzero concentration of vapor, proportionately to the concentration of vapor, wherein the housing contains the first, second and third plurality of indicators and the audible indicator.

2. The hydrocarbon detection instrument of claim 1, further comprising:
a recharger connector compatible with electrical coupling of the external power supply to the instrument, wherein the battery is rechargeable and configured to power the instrument and wherein the battery is further configured to accept recharging through the recharger connector.

3. The hydrocarbon detection instrument of claim 2, further comprising a recharging circuit configured, to apply to the rechargeable battery, a level of charging current that is applied indefinitely without appreciable shortening of battery life.

4. The hydrocarbon detection instrument of claim 1, wherein the housing provides a contiguous enclosure for a functional, self-contained instrument.

5. The hydrocarbon detection instrument of claim 1, wherein the housing further comprises a battery access port through which the battery can be removed and replaced.

6. The hydrocarbon detection instrument of claim 1, wherein the power on/off switch further comprises a battery charge enable function.

7. The hydrocarbon detection instrument of claim 1, wherein the power on/off switch is a push-type switch with alternate action.

8. The hydrocarbon detection instrument of claim 1, wherein the hydrocarbon vapor detector further comprises:
a heater, electrically connected between a first and a second terminal of the hydrocarbon vapor detector, and operable when powered, to regulate a temperature within the hydrocarbon vapor detector over at least a specified range of ambient temperatures; and
a sensor, electrically connected between a third terminal and one of the first and second terminals and having an exposed surface, having a conductivity dependent at least in part on the concentration of hydrocarbon vapor in a gas mixture contacting the exposed surface of the sensor.

9. The hydrocarbon detection instrument of claim 8, wherein the gas mixture within which the hydrocarbon vapor is present consists essentially of air.

10. The hydrocarbon detection instrument of claim 8, wherein the sensor further comprises a conductivity that increases with hydrocarbon vapor concentration.

11. The hydrocarbon detection instrument of claim 8, wherein the sensor further comprises a conductivity that increases in response to an increase in concentration of each hydrocarbon vapor that includes at least one of the following: gasoline, isobutane, propane, acetone, and acetylene.

12. The hydrocarbon detection instrument of claim 8, wherein a minimum concentration at which gasoline vapor is detected by the sensor is at least as low as five parts per million.

13. The hydrocarbon detection instrument of claim 4, further comprising a sensitivity adjustment function, wherein a plurality of settings provides a plurality of distinct thresholds at which indication of a least concentration of the hydrocarbon vapor is made.

14. The hydrocarbon detection instrument of claim 13, wherein the sensitivity adjustment function further comprises a sensitivity selection switch that provides a finite plurality of fixed, discrete, individual sensitivity settings, each setting establishing a sensitivity level in the instrument.

15. The hydrocarbon detection instrument of claim 14, wherein the setting of the sensitivity selection switch is user-positionable from outside the housing.

16. The hydrocarbon detection instrument of claim 13, wherein the sensitivity adjustment function affects both visible and audible indications of a presence of hydrocarbon vapor.

17. The hydrocarbon detection instrument of claim 1, further comprising a time delay circuit that suppresses the audible indication after application of power, with a selected duration of suppression.

18. The hydrocarbon detection instrument of claim 1, wherein the audible indicator further produces the audio signal that has a basal sound that includes a periodic sequence of short tone bursts, separated by longer silent intervals, and wherein indication of increased concentration of vapor is provided by shortening longer silent intervals separating the short tone bursts.

19. The hydrocarbon detection instrument of claim 1, wherein the first, second, and third pluralities of indicators further comprise light emitting diodes.

* * * * *